United States Patent [19]

Uemasu et al.

[11] Patent Number: 5,095,173

[45] Date of Patent: Mar. 10, 1992

[54] PROCESS FOR ISOLATING XYLENE ISOMER(S) AND/OR ETHYLBENZENE AND INCLUSION-COMPLEXING AGENT FOR USE IN ISOLATION OF XYLENE ISOMER(S) AND/OR ETHYLBENZENE

[75] Inventors: Isamu Uemasu, Tsukuba; Yosuke Takagi, Yokohama; Makoto Chiwa, Yachiyo, all of Japan

[73] Assignees: Agency of Industrial Science and Technology; Ensuiko Sugar Refining Co., Ltd.; Japan Organo Co., Ltd., all of Japan

[21] Appl. No.: 583,427

[22] Filed: Sep. 17, 1990

[30] Foreign Application Priority Data

Sep. 19, 1989 [JP] Japan ................................. 1-240807
May 14, 1990 [JP] Japan ................................. 2-121212

[51] Int. Cl.$^5$ ............................................... C07O 7/00
[52] U.S. Cl. ..................................... 585/865; 585/833; 585/864
[58] Field of Search ........................ 585/833, 864, 865

[56] References Cited

U.S. PATENT DOCUMENTS 4,153,630  5/1979  Ichikawa et al. .................... 585/867

Primary Examiner—Anthony McFarlane
Assistant Examiner—Nhat Phan
Attorney, Agent, or Firm—Sprung Horn Kramer & Woods

[57] ABSTRACT

A mixture of xylene isomers or a mixture of a xylene isomer(s) and ethylbenzene is brought into contact with at least one specific substituted α-cyclodextrin to form an inclusion complex(es) of the substituted α-cyclodextrin with a xylene isomer or ethylbenzene included therein, from which the xylene isomer(s) and/or ethylbenzene is then extracted to isolate, or separate, the same. Inclusion-complexing agents usable in isolation, or separation, of the xylene isomer(s) and/or ethylbenzene are substitited α-cyclodextrin in the form of α-cyclodextrin having the hydrogen atom of at least one hydroxyl group thereof substituted with at least one member selected from the group consisting of a glucosyl group, a maltosyl group, maltooligosaccharide residues, a hydroxyethyl group, a hydroxypropyl group, a methyl group, a sulfonic group, alkylenesulfonic groups, and carboxyalkyl groups.

1 Claim, 1 Drawing Sheet

PROCESS FOR ISOLATING XYLENE ISOMER(S) AND/OR ETHYLBENZENE AND INCLUSION-COMPLEXING AGENT FOR USE IN ISOLATION OF XYLENE ISOMER(S) AND/OR ETHYLBENZENE

BACKGROUND OF THE INVENTION

1. Field of the Invention

The present invention relates to a process for efficiently isolating, or separating, a xylene isomer(s) and/or ethylbenzene useful as a solvent and a starting material for chemical syntheses, and to an agent for use in isolation, or separation, of a xylene isomer(s) and/or ethylbenzene. Starting materials usable in the process of the present invention include mixtures of at least two xylene isomers selected from among o-xylene, m-xylene and p-xylene; and mixtures of ethylbenzene and at least one xylene isomer selected from among those mentioned above. These mixtures may further contain a small amount of impurities.

2. Prior Art

Xylenes are widely used as solvents and starting materials for chemical syntheses of synthetic resins, synthetic fibers, and the like. Among xylene isomers, p-xylene in particular is in great demand.

On the other hand, ethylbenzene is used as a starting material of styrene monomer, and the like.

Individual xylene isomers (o-isomer, m-isomer and p-isomer) are usually obtained from the so-called mixed xylene (o-isomer: about 20%, m-isomer: about 40%, p-isomer: about 15%, ethylbenzene: about 15%, other compounds such as styrene: small in amount). o-Xylene and ethylbenzene can be separated from the mixed xylene and isolated from each other by precision distillation wherein a difference in boiling point therebetween is utilized. m-Xylene and p-xylene can hardly be isolated from each other by distillation because the boiling points thereof are extremely close to each other. The common processes for isolating m-xylene and p-xylene from each other include a low-temperature processing method, an adsorption method, and an MGCC method (developed by Mitsubushi Gas Chemical Company, Inc.). The low-temperature processing method, in which a large difference in melting point between m-isomer and p-isomer is utilized, is not commonly used these days because it involves a drawback of processing at as low a temperature as $-70°$ C. and a large consumption of energy used to lower the temperature. The adsorption method, in which a zeolite molecular sieve is used as an adsorbent (UOP ISOMAR AND PAREX PROCESS developed by Universal Oil Products Co., U.S.A.), is said to provide a high yield of p-xylene having a purity of 99% or higher even when the mixed xylene is passed only once through the molecular sieve. The MGCC method, in which selective complexing of m-xylene with a mixture of hydrogen fluoride and boron trifluoride is utilized, enables pure m-xylene to be recovered in a substantial yield of 100%. Thus, the adsorption method and the MGCC method are both excellent ones. However, the former disadvantageously requires a large amount of a solvent for use in a mobile phase, while the latter involves a drawback of handling hydrogen fluoride, which is an intractable substance.

In view of the above, an object of the present invention is to provide a novel and economical process for highly selectively isolating, or separating, a xylene isomer(s) and/or ethylbenzene by using a substituted α-cyclodextrin, developed with the aim of improving the water solubility of α-cyclodextrin. Another object of the present invention is to provide an agent usable for isolation, or separation, of a xylene isomer(s) and/or ethylbenzene.

SUMMARY OF THE INVENTION

In one aspect of the present invention, there is provided a process for isolating a xylene isomer(s) and/or ethylbenzene, comprising the step of bringing a mixture containing at least two members selected from the group consisting of o-xylene, m-xylene, p-xylene, and ethylbenzene into contact with at least one substituted α-cyclodextrin in the form of α-cyclodextrin having the hydrogen atom of at least one hydroxyl group thereof substituted with at least one member selected from the group consisting of a glucosyl group a maltosyl group, maltooligosaccharide residues, a hydroxyethyl group, a hydroxypropyl group, a methyl group, a sulfonic group, alkylenesulfonic groups, and carboxyalkyl groups to form inclusion complexes of the substituted α-cyclodextrin with a xylene isomer or ethylbenzene included therein in accordance with the respective formation constants thereof; and the step of extracting the xylene isomer(s) and/or ethylbenzene from the inclusion complexes.

In another aspect of the present invention, there is provided an inclusion-complexing agent for use in isolation of a xylene isomer(s) and/or ethylbenzene, which is a substituted α-cyclodextrin in the form of α-cyclodextrin having the hydrogen atom of at least one hydroxyl group thereof substituted with at least one member selected from the group consisting of a glucosyl group, a maltosyl group, maltooligosaccharide residues, a hydroxyethyl group, a hydroxypropyl group, a methyl group, a sulfonic group, alkylenesulfonic groups, and carboxyalkyl groups.

The present invention will now be described in detail.

Agents usable for isolation, or separation, of a xylene isomer(s) and/or ethylbenzene according to the present invention are substituted α-cyclodextrins in the form of α-cyclodextrin having the hydrogen atom of at least one hydroxyl group thereof substituted with at least one member selected from the group consisting of a glucosyl group, a maltosyl group, maltooligosaccharide residues, a hydroxyethyl group, a hydroxypropyl group, a methyl group, a sulfonic group, alkylenesulfonic groups, and carboxyalkyl groups. The term "sulfonic group" as used herein is intended to encompass not only a group in the form of free acid but also groups in the form of a sodium, potassium, ammonium, lower amine, ethanolamine, or like salt thereof. The same meaning as described above in connection with the "sulfonic group" applies to the "sulfonic moiety" of the "alkylenesulfonic group" and the "carboxyl moiety" of the "carboxyalkyl group" as well. The number of carbon atoms in the alkylene moiety of the alkylenesulfonic group is preferably 1 to 5. The above-mentioned alkylene moiety may be either linear or branched. The number of carbon atoms in the carboxyalkyl group, which may be either linear or branched, is preferably 1 to 6.

These substituted α-cyclodextrins provide a remarkable merit that the inclusion complexes thereof with a xylene isomer or ethylbenzene are so high in solubility in water, as compared with those of other cyclodextrins and their substituted derivatives, that no precipitate is formed in the course of extraction thereof to enable the operation of extraction to be advantageously simplified. The use of simple α-cyclodextrin not chemically modified in isolation, or separation, of a xylene isomer(s) has already been disclosed in patent literature [see, for example, Japanese Patent Laid-Open No. 42,825/1977, titled "Process for Isolating Benzene Compound Isomer(s)"]. In this case, however, an inclusion complex(es) of α-cyclodextrin with a xylene isomer is yielded in the form of a precipitate. Accordingly, a solid liquid separation operation is required. This is the greatest drawback in carrying out the above-mentioned isolation process. While the use of the above-mentioned substituted α-cyclodextrins, e.g., glucosyl-α-cyclodextrin and maltosyl α-cyclodextrin in particular, to form inclusion complexes thereof has already been utilized in the fields of foodstuffs and the like, there are no such cases as in the present invention where the abilities of such substituted α-cyclodextrins to form inclusion complexes thereof have ever been utilized with a view to isolating a xylene isomer(s) and/or ethylbenzene.

According to the process of the present invention, a substituted α-cyclodextrin(s) as specified in the present invention is dissolved in water to prepare an aqueous solution thereof, to which a mixture of xylene isomers or a mixture of a xylene isomer(s) and ethylbenzene is then added, followed by vigorous agitation or shaking of the resultant mixture. The substituted α-cyclodextrin concentration of the above-mentioned aqueous solution is suitably 5 to 45 wt. % based on the water, preferably 10 to 25 wt. % based on the water. Additionally stated, the use of unsubstituted α-cyclodextrin or other such substituted α-cyclodextrin as to form an inclusion complex(es) thereof with a xylene isomer or ethylbenzene which has a very low solubility in water disadvantageously causes the inclusion complex(es) to precipitate in the course of formation thereof, or unfavorably compels the formation of the inclusion complex(es) to be effected in a very low unsubstituted or substituted α-cyclodextrin concentration in order to avoid the precipitation of the inclusion complex(es). By contrast, the aforementioned substituted α-cyclodextrins as specified in the present invention can be used without any such disadvantages.

The mixing ratio of the aqueous solution of the substituted α-cyclodextrin(s) to the mixture of xylene isomers or the mixture of a xylene isomer(s) and ethylbenzene may be such that the molar amount of the substituted α-cyclodextrin(s) is preferably 0.1 to 1 times as much as the total molar amount of the xylene isomer(s) and ethylbenzene, if present. The agitation or shaking may be carried out as vigorously as possible for a few minutes to several hours. The inclusion reaction may usually be effected in the range of ordinary temperature to about 45° C., and is preferably effected at around 25° C. After completion of the reaction with the agitation or shaking, oil water separation of the reaction mixture is carried out according to an appropriate method, examples of which include centrifugal separation that may be continued for 5 to 10 minutes, and other such known methods as often used in liquid-liquid extraction to improve the separability of an oil layer from a water layer, e.g., a method involving addition of a salt to a reaction mixture.

The separation of a xylene isomer(s) and/or ethylbenzene from the inclusion complex(es) dissolved in the water layer obtained through the oil-water separation may be effected by adding a relatively low boiling volatile and difficultly water-soluble organic solvent hard to include into the substituted α-cyclodextrin(s), such as diethyl ether, to the water layer and shaking the resultant mixture to extract the xylene isomer(s) and/or ethylbenzene into an organic layer. Alternatively, the aqueous solution of the inclusion complex(es) may be heated to dissociate the xylene isomer(s) and/or ethylbenzene from the inclusion complex(es), followed by extraction of the dissociated xylene isomer(s) and/or ethylbenzene with a volatile and difficultly water-soluble organic solvent of about 50° to 100° C. in boiling point hard to include into the substituted α-cyclodextrin(s), such as hexane. In either case, the resultant water layer is in the form of a transparent aqueous solution of the substituted α-cyclodextrin. The organic solvent may be vaporized from the resultant organic layer containing the xylene isomer(s) and/or ethylbenzene extracted into the organic layer to obtain the desired xylene isomer(s) and/or ethylbenzene.

When the isolation of a desired compound (xylene isomer or ethylbenzene) through the single procedure comprising the inclusion reaction and the extraction operation is so insufficient that the desired compound contains other component(s) mixed therewith in an amount unfavorable for practical use of the isolated product, repetition of the foregoing procedure comprising the inclusion reaction and the extraction operation will suffice to raise the purity of the desired compound. This will be described more specifically.

The abilities of xylene isomers and ethylbenzene to undergo inclusion reactions with the substituted α-cyclodextrins as specified in the present invention to form the corresponding inclusion complexes (in short, formation constants of inclusion comlexes) are in the order of p-xylene > ethylbenzene > m-xylene > o-xylene. Thus, a difference in formation constant of inclusion complex between components of an object mixture is utilized in the process of the present invention to separate, or isolate, and purify any one(s) of the components of the object mixture.

Accordingly, the purity of, for example, p-xylene or ethylbenzene, if not containing p-xylene, can be raised when the procedure comprising the inclusion reaction and the extraction operation according to the present invention is repeated using as a starting material the residue liquid obtained by vaporizing the organic solvent from the organic layer containing the xylene isomer(s) and/or ethylbenzene extracted thereinto and obtained using the aforementioned procedure according to the present invention. On the other hand, a larger amount of, for example, o-xylene remains in the oil layer obtained through the aforementioned oil-water separation effected after the inclusion reaction. Accordingly, the purity of o-xylene can be raised when the procedure comprising the inclusion reaction and the extraction operation according to the present invention is repeated using as a starting material the above mentioned oil layer. In either case, the number of times required to repeat the procedure comprising the inclusion reaction and the extraction operation according to the present invention to isolate one component of the object mixture as a substantially pure substance, needless to say, depends on the initial composition of the object mixture.

The molecules of the substituted α-cyclodextrin used in the process of the present invention do not undergo decomposition in themselves throughout the foregoing whole process. Accordingly, the used substituted α-cyclodextrin can be reused after recovery thereof.

The utilization of the substituted α-cyclodextrin as the inclusion complexing agent for use in the process of the present invention may be applied to isolation of a component(s) of not only the so-called mixed xylene as a mixture of all xylene isomers and ethylbenzene but also various mixtures including all possible combinations mainly composed of at least two members selected from among three xylene isomers (o-isomer, m-isomer and p-isomer) and ethylbenzene.

It will be possible to evolve the process of the present invention into a liquid-liquid chromatographic process for continuously isolating the components of a mixture containing a xylene isomer(s) and/or ethylbenzene while using as a vehicle a substituted α-cyclodextrin(s) as specified in the present invention.

BRIEF DESCRIPTION OF THE DRAWING

The foregoing and other features and advantages of the present invention will be apparent to those skilled in the art from the following detailed description of specific embodiments, taken in connection with the accompanying drawing in which:

FIGURE is a graph showing the relationship between the composition of a mixture of m-xylene and p-xylene as a starting material and the corresponding composition of an oil extract obtained through the process of the present invention in Example 6.

BEST MODES FOR CARRYING OUT THE INVENTION

Figure 1:
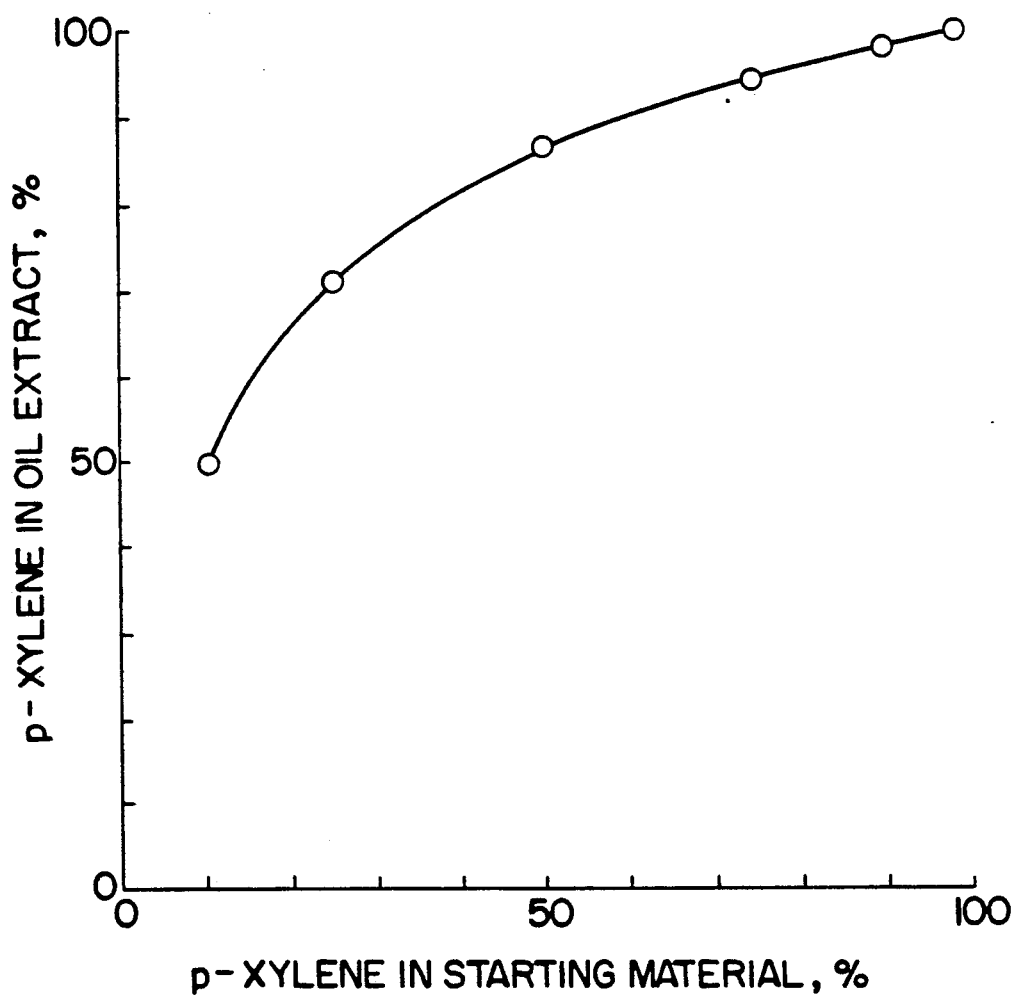

The following Examples will more specifically illustrate the present invention, but should not be construed as limiting the scope of the invention.

Example 1

0.17 g of a commercially available guaranteed reagent of xylene having a composition as listed in Table 1 was added to 5 ml of a 10 wt. % aqueous solution of monomaltosyl-α-cyclodextrin. The resultant mixture was stirred at 25° C. for one hour. Thereafter, the reaction mixture was subjected to 10 minutes of centrifugal separation at 2,500 r.p.m. The resultant water layer was separated from the organic layer, and then admixed with diethyl ether by shaking. The diethyl ether was vaporized from the resultant ether layer to obtain an organic substance.

Table 1 shows changes in the proportions of the components of the reagent in this Example, which are the results of capillary gas chromatographic analyses. The figures in Table 1 refer to the percentages of the components in terms of the percentage of the area of a peak assinged to each component based on the total area of all peaks.

TABLE 1

| Changes in Proportions of Components through Inclusion Reaction and Extraction | | |
|---|---|---|
| | Starting Material | Oil Extract |
| ethylbenzene | 16.3% | 18.0% |
| o-xylene | 21.4% | 5.0% |
| m-xylene | 44.5% | 15.8% |
| p-xylene | 17.8% | 61.2% |

EXAMPLE 2

0.24 g of a mixture of xylene isomers and ethylbenzene having a composition as listed in Table 2 was added to 5 ml of a 10 wt. % aqueous solution of monomaltosyl-α-cyclodextrin. Thereafter, substantially the same procedure as in Example 1 was repeated.

Table 2 shows changes in the proportions of the components of the mixture in this Example. In Table 2, the figures have the same meaning as in Example 1.

TABLE 2

| Changes in Proportions of Components through Inclusion Reaction and Extraction | | |
|---|---|---|
| | Starting Material | Oil Extract |
| ethylbenzene | 24.0% | 22.3% |
| o-xylene | 25.9% | 4.4% |
| m-xylene | 25.2% | 7.6% |
| p-xylene | 24.9% | 61.2% |

EXAMPLE 3

0.17 g of a mixture of ethylbenzene, o-xylene and m-xylene having a composition as listed in Table 3 was added to 5 ml of a 10 wt. % aqueous solution of monomaltosyl-α-cyclodxtrin. Thereafter, substantially the same procedure as in Example 1 was repeated.

Table 3 shows changes in the proportions of the components of the mixture in this Example. In Table 3, the figures have the same meaning as in Example 1.

TABLE 3

| Changes in Proportions of Components through Inclusion Reaction and Extraction | | |
|---|---|---|
| | Starting Material | Oil Extract |
| ethylbenzene | 32.7% | 65.2% |
| o-xylene | 34.1% | 10.2% |
| m-xylene | 33.2% | 24.6% |

EXAMPLE 4

0.17 g of a mixture of o-xylene and m-xylene having a composition as listed in Table 4 was added to 5 ml of a 10 wt. % aqueous solution of monomaltosyl-α-cyclodextrin. Thereafter, substantially the same procedure as in Example 1 was repeated.

Table 4 shows changes in the proportions of the components of the mixture in this Example. In Table 4, the figures have the same meaning as in Example 1.

TABLE 4

| Changes in Proportions of Components through Inclusion Reaction and Extraction | | |
|---|---|---|
| | Starting Material | Oil Extract |
| o-xylene | 51.2% | 27.8% |
| m-xylene | 48.8% | 72.2% |

EXAMPLE 5

0.16 g of a mixture of o-xylene, m-xylene and p-xylene having a composition as listed in Table 5 was added to 5 ml of a 10 wt. % aqueous solution of monomaltosyl-α-cyclodextrin. Thereafter, substantially the same procedure as in Example 1 was repeated.

Table 5 shows changes in the proportions of the components of the mixture in this Example. In Table 5, the figures have the same meaning as in Example 1.

TABLE 5

| Changes in Proportions of Components through Inclusion Reaction and Extraction | | |
|---|---|---|
| | Starting Material | Oil Extract |
| o-xylene | 33.7% | 5.5% |
| m-xylene | 32.2% | 8.6% |

TABLE 5-continued

Changes in Proportions of Components through Inclusion Reaction and Extraction

| | Starting Material | Oil Extract |
| --- | --- | --- |
| p-xylene | 34.1% | 85.9% |

EXAMPLE 6

0.544 g of an equimolar mixture of p-xylene and m-xylene was added to 5 g of a 10 wt. % aqueous solution of monogulcosyl-α-cyclodextrin. Thereafter, substantially the same procedure as in Example 1 was repeated.

Using each of mixtures of p-xylene and m-xylene respectively having varied p-xylene proportions of 10%, 25%, 75%, 90% and 98%, substantially the same procedure as described above was repeated.

Table 6 shows changes in the proportions of the components of the mixtures in this Example. In Table 6, the figures have the same meaning as in Example 1.

TABLE 6

Changes in Proportions of Components through Inclusion Reaction and Extraction

| | Starting Material | Oil Extract |
| --- | --- | --- |
| m-xylene | 90.0% | 50.0% |
| p-xylene | 10.0% | 50.0% |
| m-xylene | 75.0% | 28.7 |
| p-xylene | 25.0% | 71.3% |
| m-xylene | 50.0% | 12.5% |
| p-xylene | 50.0% | 87.5% |
| m-xylene | 25.0% | 5.8% |
| p-xylene | 75.0% | 94.2% |
| m-xylene | 10.0% | 2.1% |
| p-xylene | 90.0% | 97.9% |
| m-xylene | 2.0% | 0.0% |
| p-xylene | 98.0% | 100.0% |

The data in Table 6 are also summarized in FIGURE.

EXAMPLE 7

6 g of a commercially available guaranteed reagent of xylene having a composition as listed in Table 7 were added to 10 ml of a 20 wt. % aqueous solution of monogulcosyl-α-cyclodextrin. The resultant mixture was stirred at 25° C. for 2 hours, followed by oil-water separation. The included oil components present in the resultant water layer were extracted with diethyl ether, which was then distilled off to obtain 0.10 g of an oil residue containing concentrated p-xylene. Using this oil residue and 3 ml of a 20 wt. % aqueous solution of monoglucosyl α-cyclodextrin, substantially the same procedure comprising the inclusion reaction and the extraction operation as described above was repeated.

Table 7 shows changes in the proportions of the components of the reagent in this Example. In Table 7, the figures have the same meaning as in Example 1.

TABLE 7

Changes in Proportions of Components through Inclusion Reaction and Extraction

| | Starting Material | First Oil Extract | Second Oil Extract |
| --- | --- | --- | --- |
| ethylbenzene | 17.1% | 21.4% | 5.3% |
| o-xylene | 20.5% | 2.7% | 0% |
| m-xylene | 43.3% | 16.3% | 0.4% |
| p-xylene | 19.1% | 59.6% | 94.3% |

EXAMPLE 8

3.0 g of a commercially available guaranteed reagent of xylene having a composition as listed in Table 8 were added to 10 ml of a 20 wt. % aqueous solution of a mixture of maltosyl-α-cyclodextrins (containing as the main ingredients 41 wt. % of monomaltosyl-α-cyclodextrin and 43 wt. % of dimaltosyl-α-cyclodextrins). The resultant mixture was stirred at 25° C. for 5 minutes. Thereafter, substantially the same procedure as in Example 1 was repeated.

Table 8 shows changes in the proportions of the components of the reagent in this Example. In Table 8, the figures have the same meaning as in Example 1.

TABLE 8

Changes in Proportions of Components through Inclusion Reaction and Extraction

| | Starting Material | Oil Extract |
| --- | --- | --- |
| ethylbenzene | 17.1% | 22.8% |
| o-xylene | 20.5% | 3.2% |
| m-xylene | 43.3% | 14.4% |
| p-xylene | 19.1% | 59.6% |

According to the present invention, a component(s) of a mixture of xylene isomers or a mixture of a xylene isomer(s) and ethylbenzene can be highly selectively isolated, or separated, through an inclusion reaction(s) and an extraction operation(s).

A substituted α-cyclodextrin(s) after extraction therefrom of a desired compound(s) can be repeatedly used in the inclusion reaction(s) and the extraction operation(s). This, coupled with the simplicity of the extraction operation in the process of the present invention, can reduce the cost of isolation, or separation, of the xylene isomer(s) and/or ethylbenzene.

What is claimed is:

1. A process for isolating a xylene isomer(s) and/or ethylbenzene, comprising the step of bringing a mixture containing at least two members selected from the group consisting of o-xylene, m-xylene, p-xylene, and ethylbenzene into contact with at least one substituted α-cyclodextrin in the form of α-cyclodextrin having the hydrogen atom of at least one hydroxyl group thereof substituted with at least one member selected from the group consisting of a glucosyl group, a maltosyl group, maltooligosaccharide residues, a hydroxyethyl group, a hydroxypropyl group, a methyl group, a sulfonic group, alkylenesulfonic groups, and carboxyalkyl groups to form inclusion complexes of said substituted α-cyclodextrin with a xylene isomer or ethylbenzene; and the step of extracting said xylene isomer(s) and/or ethylbenzene from said inclusion complexes.

* * * * *

UNITED STATES PATENT AND TRADEMARK OFFICE
CERTIFICATE OF CORRECTION

PATENT NO. : 5,095,173

DATED : March 10, 1992

INVENTOR(S) : Uemasu et al.

It is certified that error appears in the above-identified patent and that said Letters Patent is hereby corrected as shown below:

| | |
|---|---|
| On title page add the following | U.S. PATENT DOCUMENTS: Insert -- 3,465,055, 9/1969, Gleim et al......585/865; 3,456,028, 9/1969, Gerhold et al.....585/840 -- |
| Title Page | Insert -- FOREIGN PATENT DOCUMENTS: 5242825... Japan 1977-- |

Signed and Sealed this

Fifth Day of October, 1993

Attest:

BRUCE LEHMAN

*Attesting Officer*  *Commissioner of Patents and Trademarks*